(12) United States Patent
Haneda et al.

(10) Patent No.: US 12,157,875 B2
(45) Date of Patent: Dec. 3, 2024

(54) SCAFFOLDING MATERIAL FOR CELL CULTURES AND CELL CULTURE METHOD USING SAME

(71) Applicant: SEKISUI CHEMICAL CO., LTD., Osaka (JP)

(72) Inventors: Satoshi Haneda, Osaka (JP); Yuriko Manabe, Osaka (JP); Ryoma Ishii, Osaka (JP); Hiroki Iguchi, Osaka (JP); Hiroshi Yamauchi, Osaka (JP); Takahiro Omura, Saitama (JP)

(73) Assignee: SEKISUI CHEMICAL CO., LTD., Osaka (JP)

(*) Notice: Subject to any disclaimer, the term of this patent is extended or adjusted under 35 U.S.C. 154(b) by 569 days.

(21) Appl. No.: 16/919,452

(22) Filed: Jul. 2, 2020

(65) Prior Publication Data
US 2020/0399576 A1 Dec. 24, 2020

Related U.S. Application Data

(63) Continuation-in-part of application No. 16/958,182, filed as application No. PCT/JP2018/048389 on Dec. 27, 2018.

(30) Foreign Application Priority Data

Dec. 27, 2017 (JP) ................. 2017-252420

(51) Int. Cl.
*C12M 1/12* (2006.01)
*C08F 118/10* (2006.01)
(Continued)

(52) U.S. Cl.
CPC ........... *C12M 25/14* (2013.01); *C08F 118/10* (2013.01); *C08F 216/06* (2013.01); *C12N 5/0068* (2013.01); *C12N 2533/30* (2013.01)

(58) Field of Classification Search
CPC ...... C12M 25/14; C12M 25/02; C12M 23/20; C12N 5/0068; C12N 2533/30;
(Continued)

(56) References Cited

U.S. PATENT DOCUMENTS 4,537,790 A  8/1985  Horodniceanu et al.
5,393,668 A  2/1995  Cinatl et al.
(Continued)

FOREIGN PATENT DOCUMENTS

CN  1216581  5/1999
CN  101528822  9/2009
(Continued)

OTHER PUBLICATIONS

Machine Translation of KR 20070122519 A (Year: 2023).*
(Continued)

*Primary Examiner* — Michael L Hobbs
(74) *Attorney, Agent, or Firm* — WENDEROTH, LIND & PONACK, L.L.P.

(57) ABSTRACT

A scaffolding material for culturing a cell, the scaffolding material for culturing a cell containing a synthetic resin, and having a nitrogen content of the synthetic resin of 0.1% by mass or more and 10% by mass or less. According to the scaffolding material for cell culture, the scaffolding material can have suitable hydrophilicity and strength, high fixation of cells after seeding, and highly efficient cell proliferation.

11 Claims, 6 Drawing Sheets

(51) Int. Cl.
*C08F 216/06* (2006.01)
*C12N 5/00* (2006.01)

(58) Field of Classification Search
CPC .... C08F 114/10; C08F 216/06; C08F 216/38; C08F 8/28; C09D 129/14
See application file for complete search history.

(56) References Cited

U.S. PATENT DOCUMENTS

| | | | |
|---|---|---|---|
| 5,880,216 | A | 3/1999 | Tanihara et al. |
| 6,984,692 | B2 | 1/2006 | Kumaki et al. |
| 8,153,715 | B2 | 4/2012 | Stark |
| 2002/0161440 | A1* | 10/2002 | Son ............... A61L 15/28 602/49 |
| 2005/0164377 | A1 | 7/2005 | Miyabayashi et al. |
| 2007/0122901 | A1 | 5/2007 | Morita et al. |
| 2009/0130756 | A1* | 5/2009 | Klann ............... A61K 9/146 435/395 |
| 2009/0176937 | A1 | 7/2009 | Frank et al. |
| 2011/0129924 | A1 | 6/2011 | Ying et al. |
| 2011/0318829 | A1 | 12/2011 | Tazaki et al. |
| 2012/0015177 | A1 | 1/2012 | Kim |
| 2012/0202070 | A1 | 8/2012 | Asanuma et al. |
| 2013/0280725 | A1 | 10/2013 | Ismagilov et al. |
| 2013/0309679 | A1 | 11/2013 | Ismagilov et al. |
| 2014/0210338 | A1 | 7/2014 | Matsumura et al. |
| 2014/0315235 | A1* | 10/2014 | Puschmann ........ G01N 33/5058 435/29 |
| 2015/0010919 | A1 | 1/2015 | Feinberg et al. |
| 2015/0140652 | A1 | 5/2015 | Sasai et al. |
| 2018/0126713 | A1 | 5/2018 | Glaser et al. |
| 2018/0194935 | A1* | 7/2018 | Maeda ............... C08F 8/28 |
| 2019/0106561 | A1 | 4/2019 | Ukidwe |
| 2020/0362289 | A1 | 11/2020 | Haneda et al. |
| 2020/0399576 | A1 | 12/2020 | Haneda et al. |
| 2020/0407672 | A1 | 12/2020 | Haneda et al. |
| 2021/0071147 | A1 | 3/2021 | Haneda et al. |
| 2022/0227898 | A1 | 7/2022 | Iguchi et al. |

FOREIGN PATENT DOCUMENTS

| | | | |
|---|---|---|---|
| CN | 104428651 | | 3/2015 |
| CN | 107406652 | | 11/2017 |
| EP | 0339371 | | 11/1989 |
| EP | 0 897 000 | | 2/1999 |
| EP | 2 385 105 | | 11/2011 |
| EP | 2 821 789 | | 1/2015 |
| EP | 3 733 834 | | 11/2020 |
| EP | 4 286 508 | | 12/2023 |
| JP | H0551243 A * | 3/1993 | ............ C03C 27/12 |
| JP | 6-153905 | | 6/1994 |
| JP | 9-131397 | | 5/1997 |
| JP | 10-52268 | | 2/1998 |
| JP | 10-204204 | | 8/1998 |
| JP | 2001-89574 | | 4/2001 |
| JP | 2001-131325 | | 5/2001 |
| JP | 2006-42758 | | 2/2006 |
| JP | 2006-272002 | | 10/2006 |
| JP | 2006-314285 | | 11/2006 |
| JP | 2006314285 A * | 11/2006 | ............ C12M 23/20 |
| JP | 2009-39138 | | 2/2009 |
| JP | 2009-273444 | | 11/2009 |
| JP | 2010-91689 | | 4/2010 |
| JP | 2010-158180 | | 7/2010 |
| JP | 2010-168444 | | 8/2010 |
| JP | 4956753 | | 6/2012 |
| JP | 2015-142525 | | 8/2015 |
| JP | 2015-195752 | | 11/2015 |
| JP | 2015-199932 | | 11/2015 |
| JP | 2015-205462 | | 11/2015 |
| JP | 2016-186044 | | 10/2016 |
| JP | 2017-23008 | | 2/2017 |
| JP | 2017-46676 | | 3/2017 |
| JP | 6144437 | | 6/2017 |
| JP | 2017-163898 | | 9/2017 |
| JP | 6427450 | | 11/2018 |
| JP | 6427450 B2 * | 11/2018 | ............ C08F 216/38 |
| JP | 2019-115322 | | 7/2019 |
| JP | 2019-115323 | | 7/2019 |
| JP | 2019-118345 | | 7/2019 |
| KR | 20070122519 A * | 12/2007 | ............ A61K 47/00 |
| TW | 201540829 | | 11/2015 |
| WO | 97/41216 | | 11/1997 |
| WO | 01/05877 | | 1/2001 |
| WO | 2006/093207 | | 9/2006 |
| WO | 2012/023518 | | 2/2012 |
| WO | 2013/183777 | | 12/2013 |
| WO | 2015/129837 | | 9/2015 |
| WO | 2016/122123 | | 8/2016 |
| WO | WO-2017057663 A1 * | 4/2017 | ............... C08F 8/28 |
| WO | 2019/131978 | | 7/2019 |
| WO | 2019/131981 | | 7/2019 |
| WO | 2019/131982 | | 7/2019 |
| WO | WO-2021023518 A1 * | 2/2021 | ............ H04W 16/14 |

OTHER PUBLICATIONS

Machine Translation of JP 2006314285 A. (Year: 2023).*
Machine Translation of JP H0551243 A (Year: 2024).*
Translation of The International Preliminary Report on Patentability issued Jul. 9, 2020 in International (PCT) Application No. PCT/JP2018/048389.
Translation of The International Preliminary Report on Patentability issued Jul. 9, 2020 in International (PCT) Application No. PCT/JP2018/048391.
Translation of The International Preliminary Report on Patentability issued Jul. 2, 2020 in International (PCT) Application No. PCT/JP2018/048386.
Extended European Search Report issued Oct. 12, 2021 in corresponding European Patent Application No. 18893580.3, 8 pages.
International Search Report issued Apr. 2, 2019 in International (PCT) Application No. PCT/JP2018/048389.
Bayramoglu et al., "Preparation and Characterization of Poly(hydroxyethyl methacrylate-co-poly(ethyl-eneglycol-methacrylate)/Hydroxypropyl-chitosan) Hydrogel Films: Adhesion of Rat Mesenchymal Stem Cell," Macromolecular Research, 2011, vol. 19, No. 4, pp. 385-395.
Rebollar et al., "Physicochemical modifications accompanying UV laser induced surface structures on poly(ethyleneterephthalate) and their effect on adhesion of mesenchymal cell," Phys. Chem. Chem. Phys., 2014, vol. 16, pp. 17551-17559.
Togami et al., "Effects of water holding capability of the PVF sponge on the adhesion and differentiation of rat bone marrow stem cell culture," Society For Biomaterials, 2013, vol. 102A, No. 1, pp. 247-253.
Saha et al., "Surface-engineered substrates for improved human pluripotent stem cell culture under fully defined conditions," PNAS, 2011, vol. 108, No. 46, pp. 18714-18719.
Tunma et al., "Improving the attachment and proliferation of umbilical cord mesenchymal stem cells on modified polystyrene by nitrogen-containing plasma," Cytotechnology, 2013, vol. 65, pp. 119-134.
Togami et al., "Effects of the water-holding capability of polyvinyl formal sponges on osteogenic ability in in vivo experiments," Society For Biomaterials, 2014, vol. 103B Issue 1, pp. 188-194.
Miyoshi et al., "Three-dimensional culture of mouse bone marrow cells within a porous polymer scaffold: effects of oxygen concentration and stromal layer on expansion of haematopoietic progenitor cells," Journal of Tissue Engineering and Regenerative Medicine, 2011, vol. 5, pp. 112-118.
Notice of Ground of Rejection mailed on Apr. 14, 2020 in Japanese Patent Application No. 2019-562491 with English-language translation.
Office Action issued Jan. 20, 2023 in U.S. Appl. No. 16/958,204, 22 pages.
Office Action issued Jan. 26, 2023 in U.S. Appl. No. 16/958,182, 28 pages.

(56) References Cited

OTHER PUBLICATIONS

Poly(vinylamine), Polymer source, Inc., downloaded on Jan. 19, 2023 from www.polymersource.ca/index.php?route=product, one page (Year: 2023).
Extended European Search Report issued Oct. 8, 2021 in corresponding European Patent Application No. 18897018.0, 8 pages.
Office Action issued Sep. 21, 2022 in U.S. Appl. No. 16/958,218, 15 pages.
First Examination Report issued Jun. 14, 2022 in corresponding Indian Patent Application No. 202047029411, 7 pages.
Extended European Search Report issued Dec. 23, 2021 in corresponding European Patent Application No. 18893713.0, 7 pages.
Office Action dated Mar. 31, 2022 in corresponding U.S. Appl. No. 16/958,218, filed Jun. 26, 2020, 19 pages.
Office Action issued Apr. 12, 2023, in U.S. Appl. No. 16/958,218, 18 pages.
Office Action issued Jun. 27, 2023 in U.S. Appl. No. 16/958,182, 18 pages.
Lee et al., "Cell Behavior on Polymer Surfaces With Different Functional Groups", Science and Technology of Polymers and Advanced Materials, Edited by P.N. Prasad et al., Plenum Press, New York, p. 535-545 (Year: 1998), 11 pages.
Office Action issued Jul. 12, 2023 in U.S. Appl. No. 16/919,312, 28 pages.
Office Action issued Aug. 14, 2023 in corresponding U.S. Appl. No. 16/958,204.
Official Communication dated Sep. 18, 2023 issued in corresponding Indian Patent Application No. 202047029416, 2 pages.
Office Action issued Oct. 13, 2023 in U.S. Appl. No. 16/958,218.
Examination report No. 1 issued Nov. 1, 2023 in Australian Patent Application No. 2018398052.
Extended European Search Report issued Jan. 31, 2024 in corresponding European Patent Application No. 23203425.6.
Office Action issued Mar. 4, 2024 in U.S. Appl. No. 16/919,312, 21 pages.
Examination report issued Nov. 16, 2023 in corresponding Australian Patent Application No. 2018398050, 3 pages.
Meng Zhong Wang., "Handbook of Adhesive Application", p. 16-20, Chemical Industry Press, publication date: Nov. 30, 1987.
Office Action issued May 8, 2024 in related U.S. Appl. No. 16/958,218, 20 pages.
Mengzhong et al.., "Handbook of Adhesive Application", p. 16-20, Chemical Industry Press, publication date: Nov. 30, 1987, with English translation, 12 pages.
Office Action issued Jun. 17, 2024, in related U.S. Appl. No. 16/958,204.
Chen Huipeng (ed.), "Advances in Pharmaceutical Bioengineering", People's Military Medical Press, Jul. 2004, p. 259, with English-language translation.
Wang Yingjun (ed), "Biomedical Ceramic Materials", South China University of Technology Press, Oct. 2010, pp. 167-168, with English-language translation.
Office Action issued Oct. 4, 2024 in U.S. Appl. No. 16/958,218.

\* cited by examiner

[FIG. 2]
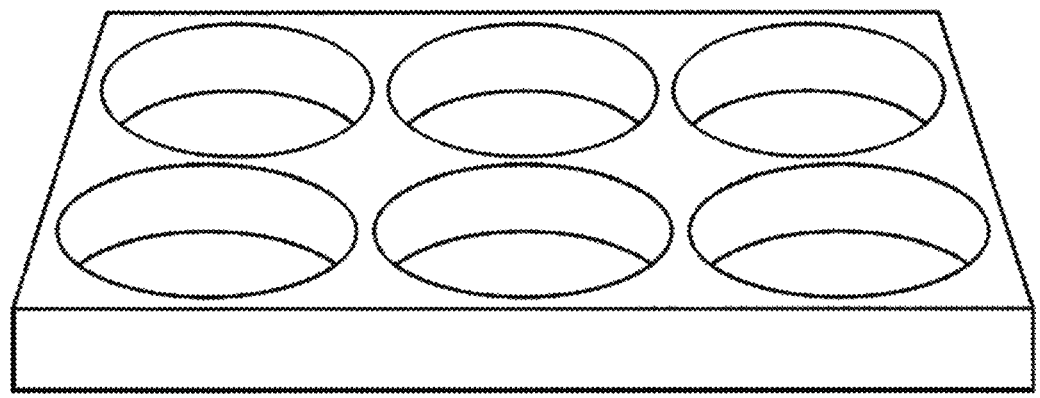

SCAFFOLDING MATERIAL FOR CELL CULTURES AND CELL CULTURE METHOD USING SAME

BACKGROUND OF THE INVENTION

Field of the Invention

The present invention relates to a scaffolding material for cell culture and a cell culture method using the same.

Description of the Related Art

Stem cells are expected to be applied on drug discovery and regenerative medicine. Stem cells are cells that have self-renew potency and differentiation potency, including pluripotent stem cells that can differentiate into all cell types, and tissue stem cells and tissue progenitor cells that can differentiate only into constituent cell types of the body tissue in the same series. Examples of the pluripotent stem cells include human pluripotent stem cells (hPSCs) such as human embryonic stem cells (hESCs) and human induced pluripotent stem cells (hiPSCs). It is an essential basic technology to cultivate and proliferate stem cells safely and with good reproducibility for medical application of these cells. In particular, for industrial application on regenerative medicine, it is necessary to handle a large amount of stem cells in an undifferentiated state. Accordingly, extensive studies have been conducted on techniques for proliferating stem cells using natural and synthetic macromolecules and feeder cells, and maintaining the pluripotency (or multipotency). In particular, it is known that cell fixation after seeding is extremely high when an adhesive protein such as laminin or vitronectin, or a matrigel derived from mouse sarcoma is used as a natural polymer.

However, there are problems in that natural polymers are expensive because of their very low productivity, variations between lots can be seen because they are naturally occurring substances, and there are safety concerns due to animal-derived components.

In order to solve the above problems, a stem cell culture resin carrier using a synthetic resin has been proposed. For example, the column of Examples in Patent Document 1 discloses a polyvinyl acetal compound having a degree of acetalization of 20 to 60 mol % in order to provide a scaffold having excellent hydrophilicity and water resistance in culturing mouse fibroblasts. The column of Examples in Patent Document 2 discloses a hydrogel composed of an acrylic polymer in culturing mouse ES cells. The column of Examples in Patent Document 3 discloses a hydrophilic and flexible polyrotaxane gel in culturing mouse iPS cells.

RELATED ART DOCUMENT

Patent Document

Patent Document 1: JP 2006-314285 A
Patent Document 2: JP 2010-158180 A
Patent Document 3: JP 2017-23008 A

SUMMARY OF THE INVENTION

Problems to be Solved by the Invention

However, Patent Document 1 has a problem in that the scaffolding material resin is swelled in a medium due to its high hydrophilicity, and thus is peeled off. In addition, there is a problem in that the fixation of stem cells or pluripotent stem cells after seeding is so low that the cells do not proliferate sufficiently. In Patent Document 2, sodium 2-acrylamido-2-methylpropane sulfonate, sodium p-styrene sulfonate and N,N'-dimethylacrylamide are used, so that there is a problem in that the scaffolding material resin is swelled in a medium due to its high hydrophilicity, and thus is peeled off. Patent Document 3 has a problem in that the scaffolding material resin is swelled in a medium due to its high hydrophilicity, and thus is peeled off. There is a problem in that the scaffolding material is so flexible that differentiation into cardiomyocytes is promoted.

In addition, such a conventional scaffolding material for cell culture has a problem in that even when cells other than stem cells are used, the fixability after seeding is so low that the cells do not proliferate sufficiently.

As described above, there have been needs of a scaffolding material for cell culture having suitable hydrophilicity and strength, and a cell culture method using the same.

An object of the present invention is to provide a scaffolding material for cell culture having suitable hydrophilicity and strength, high fixation of cells after seeding, and highly efficient cell proliferation, and a cell culture method using the same.

Means for Solving the Problems

The present invention relates to the followings.

(1) A scaffolding material for culturing a cell, the scaffolding material for culturing a cell containing a synthetic resin, and having a nitrogen content of the synthetic resin of 0.1% by mass or more and 10% by mass or less.

(2) The scaffolding material for culturing a cell according to (1), in which the synthetic resin contains a Bronsted basic group in an amount of 1 mol % or more and 50 mol % or less.

(3) The scaffolding material for culturing a cell according to (2), in which the compound having a Bronsted basic group is an amine-based basic group.

(4) The scaffolding material for culturing a cell according to (2), in which the synthetic resin contains at least one selected from the group consisting of a structural unit having an amine structure, a structural unit having an imine structure and a structural unit having an amide structure.

(5) The scaffolding material for culturing a cell according to (1), in which the synthetic resin contains a structural unit having an amide structure.

(6) The scaffolding material for culturing a cell according to (1), in which the synthetic resin contains both of a structural unit having an imine structure and a structural unit having an amine structure.

(7) The scaffolding material for culturing a cell according to (1), in which the synthetic resin contains a polyvinyl acetal resin having a degree of acetalization of 54 mol % or more.

(8) The scaffolding material for culturing a cell according to (1), in which the synthetic resin contains a polyvinyl butyral resin.

(9) A container for culturing a cell including the scaffolding material for culturing a cell according to (1).

(10) A carrier for culturing a cell, containing
the scaffolding material for culturing a cell according to (1), and
a polysaccharide.

(11) A fiber for culturing a cell, including the scaffolding material for culturing a cell according to (1).

(12) A method for culturing cells using the scaffolding material for culturing a cell according to (1).

Effect of the Invention

According to the present invention, there are provided a scaffolding material for cell culture having suitable hydrophilicity and strength, and high fixation of cells after seeding, and a cell culture method using the same.

BRIEF DESCRIPTION OF THE DRAWINGS

FIG. 2 is a schematic perspective view of the 6-well type container for cell culture according to an embodiment;

DETAILED DESCRIPTION OF THE PREFERRED EMBODIMENTS

Figure 1A:
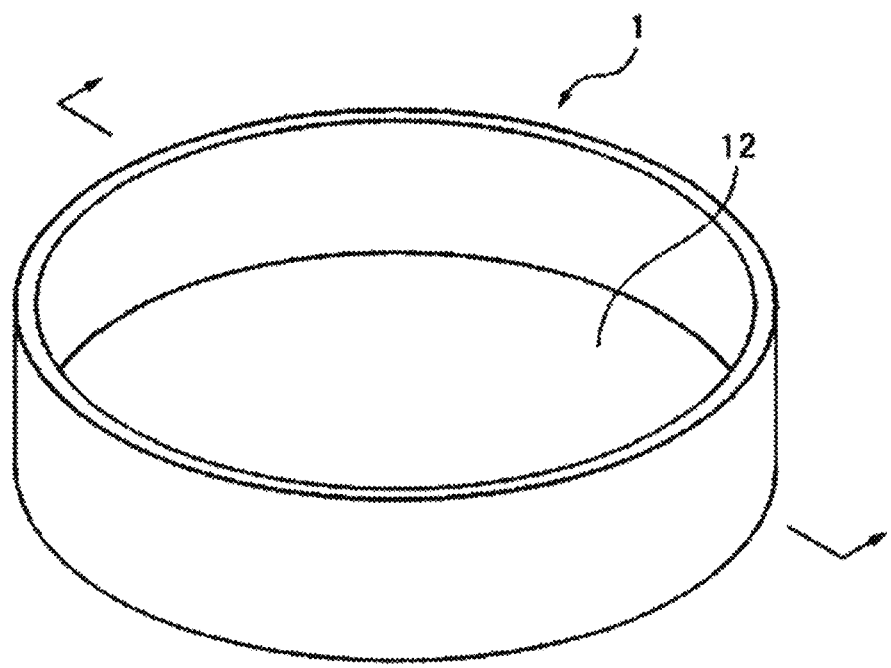
FIG. 1A is a schematic perspective view of the container for cell culture according to an embodiment.

Hereinafter, a description is made of the present invention with reference to embodiments, but the present invention is not limited to the following embodiments.

Scaffolding Material for Cell Culture

As a result of intensive studies, the present inventors have found that the above problems can be solved by using a synthetic resin having a nitrogen content of 0.1% or more and 10% or less, and thus have completed the present invention.

In other words, the present invention relates to a scaffolding material for cell culture containing a synthetic resin, wherein the nitrogen content of the synthetic resin is 0.1% or more and 10% or less.

The nitrogen content is more preferably 0.3% by mass or more and 8% by mass or less, still more preferably 0.5% by mass or more and 5% by mass or less. The synthetic resin preferably contains a Bronsted basic group in an amount of 1 mol % or more and 50 mol % or less, more preferably 1 mol % or more and 30 mol % or less.

The elemental composition of the obtained synthetic resin can be analyzed by X-ray photoelectron spectroscopy (apparatus: multifunctional scanning X-ray photoelectron spectrometer (XPS), PHI 5000 VersaProbe III, manufactured by ULVAC-PHI, Inc.). The total amount of all the detected elements is defined as 100%, and the occupation rate (%) of nitrogen in all the elements is defined as the nitrogen content.

The scaffolding material for cell culture of the present invention includes an aspect in which the material is composed of only a synthetic resin.

The scaffolding material for cell culture has so suitable hydrophilicity and strength that the fixation of cells after seeding is improved. In particular, in a serum-free medium culture containing no feeder cell or adhesive protein, the initial fixation rate of cells after seeding is improved.

The scaffolding material for cell culture is not particularly limited for component as long as the above-mentioned requirements are satisfied, but preferably contains a synthetic resin.

The synthetic resin refers to a resin mainly composed of a polymer (hereinafter, also simply referred to as "polymer") obtained by polymerizing (including polycondensing) a polymerizable monomer (hereinafter, also simply referred to as "monomer"). The polymer may be a homopolymer obtained by polymerizing only one type of monomer, or a copolymer obtained by polymerizing two or more types of monomers.

Examples of the polymer include a polymer composed of one or more polymerizable monomers of saturated or unsaturated hydrocarbons, aromatic hydrocarbons, saturated or unsaturated fatty acids, aromatic carboxylic acids, saturated or unsaturated ketones, aromatic ketones, saturated or unsaturated alcohols, aromatic alcohols, saturated or unsaturated amines, aromatic amines, saturated or unsaturated thiols, aromatic thiols and organosilicon compounds.

Specific examples of the polymer include polyolefin, polyether, polyvinyl alcohol, polyvinyl acetal, polyester, poly(meth)acrylic ester, epoxy resin, polyamide, polyimide, polyurethane, polycarbonate, cellulose and polypeptide.

From the viewpoint of further enhancing the fixation of cells, the synthetic resin preferably has at least one skeleton of a polyvinyl acetal skeleton and a poly(meth)acrylic ester skeleton, and a polyvinyl acetal resin is preferable.

From the viewpoint of further enhancing the fixation of cells, the polymer is preferably a poly(meth)acrylic ester or a polyvinyl acetal resin, and a polyvinyl acetal resin is more preferable.

These polymers may be used alone or in combination of two or more. When two or more polymers are combined, they may be used as a mixture, or may be used as a polymer in which the skeletons of the two or more polymers are chemically bonded. Accordingly, when a plurality of them are combined as a synthetic resin, it is preferable to combine poly(meth)acrylic ester and polyvinyl acetal.

In the present specification, "(meth)acrylate" refers to at least one selected from the group consisting of (meth)acrylic ester and (meth)acrylic acid. In addition, poly(meth)acrylate is not only polymers obtained by polymerizing a monomer, (meth)acrylic ester or (meth)acrylic acid, but also includes those obtained by copolymerizing a monomer in addition to (meth)acrylic ester or (meth)acrylic acid.

The (meth)acrylic ester is not particularly limited, but preferably contains at least one selected from alkyl (meth)acrylic esters, cyclic alkyl (meth)acrylic esters, aryl (meth)acrylic esters, (meth)acrylamides, polyethylene glycol (meth)acrylates and phosphorylcholine (meth)acrylates.

Examples of the alkyl (meth)acrylic ester include methyl (meth) acrylate, ethyl (meth) acrylate, n-propyl (meth)acrylate, isopropyl (meth)acrylate, n-butyl (meth)acrylate, isobutyl (meth)acrylate, t-butyl (meth)acrylate, n-octyl (meth)acrylate, isooctyl (meth)acrylate, 2-ethylhexyl (meth)acrylate, nonyl (meth)acrylate, isononyl (meth)acrylate, decyl (meth)acrylate, isodecyl (meth)acrylate, lauryl (meth)acrylate, stearyl (meth)acrylate and isotetradecyl (meth)acrylate.

These alkyl (meth)acrylic esters are not particularly limited, but may be substituted with various substituents including an alkoxy group having 1 to 3 carbon atoms and a tetrahydrofurfuryl group. Examples include methoxyethyl acrylate and tetrahydrofurfuryl acrylate.

Examples of the cyclic alkyl (meth)acrylic ester include cyclohexyl (meth)acrylate and isobornyl (meth) acrylate.

Examples of the aryl (meth)acrylic ester include phenyl (meth)acrylate and benzyl (meth)acrylate.

Examples of the acrylamide include (meth)acrylamide, N-isopropyl (meth) acrylamide, N-tert-butyl (meth) acrylamide, N,N'-dimethyl (meth)acrylamide, (3-(meth)acrylamidopropyl) trimethylammonium chloride, 4-(meth)acryloylmorpholine, 3-(meth) acryloyl-2-oxazolidinone, N-[3-(dimethylamino) propyl] (meth) acrylamide, N-(2-hydroxyethyl) (meth)acrylamide, N-methylol (meth) acrylamide and 6-(meth)acrylamidohexanoic acid.

Examples of the polyethylene glycol (meth)acrylate include methoxy-polyethylene glycol (meth)acrylate, ethoxy-polyethylene glycol (meth)acrylate, hydroxy-polyethylene glycol (meth)acrylate, methoxy-diethylene glycol (meth) acrylate, ethoxy-diethylene glycol (meth) acrylate, hydroxy-diethylene glycol (meth)acrylate, methoxy-triethylene glycol (meth)acrylate, ethoxy-triethylene glycol (meth)acrylate and hydroxy-triethylene glycol (meth)acrylate.

Examples of the phosphorylcholine (meth)acrylate include 2-(meth)acryloyloxyethyl phosphorylcholine.

Monomers other than the (meth)acrylic esters are not particularly limited, but include (meth)acrylic acids, ethylene and vinyl esters.

The (meth)acrylic esters may be used alone or in combination of two or more. In this specification, the (meth)acrylic acid is a generic term for acrylic acid and methacrylic acid, and the (meth)acrylate is a generic term for acrylate and methacrylate.

Among the synthetic resins, it is preferable to use a polyvinyl acetal resin. Hereinafter, a description is made of the polyvinyl acetal resin.

Polyvinyl Acetal Resin

The polyvinyl acetal resin is a resin synthesized by acetalizing polyvinyl alcohol with an aldehyde, which resin has an acetyl group, a hydroxyl group and an acetal group on the side chain. The polyvinyl acetal resin may be a modified polyvinyl acetal resin having another substituent (a substituent other than an acetyl group, a hydroxyl group and an acetal group) on the side chain. As the other substituent, a substituent having a Bronsted basic group described below is preferable.

The aldehydes for use in acetalization include aldehydes having a chain aliphatic group, a cyclic aliphatic group or an aromatic group having 1 to 10 carbon atoms. As the aldehydes, conventionally publicly known aldehydes can be used.

The type of the aldehyde is not particularly limited, but includes formaldehyde, acetaldehyde, propionaldehyde, butyraldehyde, pentanal, hexanal, heptanal, octanal, nonanal, decanal, acrolein, benzaldehyde, cinnamaldehyde, perylaldehyde, formylpyridine, formylimidazole, formylpyrrole, formylpiperidine, formylpiperidine, formyltriazole, formyltetrazole, formylindole, formylisoindole, formylpurine, formylpurine, formylbenzimidazole, formylbenzotriazole, formylquinoline, formylisoquinoline, formylquinoxaline, formylcinnoline, formylpteridine, formylfuran, formyloxolane, formyloxane, formylthiophene, formylthiolane, formylthiane, formyladenine, formylguanine, formylcytosine, formylthymine and formyluracil. The aldehyde may be a chain or cyclic one.

The aldehyde is preferably formaldehyde, acetaldehyde, propionaldehyde, butyraldehyde or pentanal, more preferably butyraldehyde. Accordingly, the polyvinyl acetal resin is more preferably a polyvinyl butyral resin.

The addition amount of the aldehyde can be appropriately set according to the desired amount of the acetal group. In particular, it is preferable that the addition amount of the aldehyde is 60 to 95 mol %, preferably 65 to 90 mol % with respect to 100 mol % polyvinyl alcohol, because the acetalization reaction is efficiently performed and unreacted aldehydes are easily removed.

The polyvinyl alcohol may be a copolymer with a vinyl compound. The vinyl compound includes ethylene, vinylamine, allylamine, vinylpyrrolidone, maleic anhydride, maleimide, itaconic acid and (meth)acrylic acids. The vinyl compound may be used alone or in combination of two or more.

The copolymer may be a block copolymer of a polyvinyl acetal resin and a vinyl compound, or a graft copolymer in which a vinyl compound is grafted to a polyvinyl acetal resin. The copolymer is preferably a graft copolymer.

The copolymer can be synthesized, for example, by any of the following methods (1) to (3). (1) A method for synthesizing a polyvinyl acetal resin including using polyvinyl alcohol in which a vinyl compound is copolymerized. (2) A method for synthesizing a polyvinyl acetal resin including using polyvinyl alcohol and polyvinyl alcohol in which a vinyl compound is copolymerized. (3) A method including graft-copolymerizing a vinyl compound to a pre-graft-copolymerized polyvinyl acetal resin.

For the (meth)acrylic acids, the (meth)acrylic ester is not particularly limited, but preferably contains at least one selected from alkyl (meth)acrylic esters, cyclic alkyl (meth)acrylic esters, aryl (meth)acrylic esters, (meth)acrylamides, polyethylene glycol (meth)acrylates and phosphorylcholine (meth) acrylates.

Examples of the alkyl (meth)acrylic ester include methyl (meth) acrylate, ethyl (meth) acrylate, n-propyl (meth)acrylate, isopropyl (meth)acrylate, n-butyl (meth)acrylate, isobutyl (meth)acrylate, t-butyl (meth)acrylate, n-octyl (meth)acrylate, isooctyl (meth)acrylate, 2-ethylhexyl (meth) acrylate, nonyl (meth)acrylate, isononyl (meth)acrylate, decyl (meth)acrylate, isodecyl (meth)acrylate, lauryl (meth) acrylate, stearyl (meth)acrylate and isotetradecyl (meth) acrylate.

Examples of the cyclic alkyl (meth)acrylic ester include cyclohexyl (meth)acrylate and isobornyl (meth) acrylate.

Examples of the aryl (meth)acrylic ester include phenyl (meth)acrylate and benzyl (meth)acrylate.

Examples of the acrylamide include (meth)acrylamide, N-isopropyl (meth) acrylamide, N-tert-butyl (meth) acrylamide, N,N'-dimethyl (meth)acrylamide, (3-(meth)acrylamidopropyl) trimethylammonium chloride, 4-(meth)acryloylmorpholine, 3-(meth) acryloyl-2-oxazolidinone, N-[3-(dimethylamino) propyl] (meth) acrylamide, N-(2-hydroxyethyl) (meth)acrylamide, N-methylol (meth) acrylamide and 6-(meth)acrylamidohexanoic acid.

Examples of the polyethylene glycol (meth)acrylate include methoxy-polyethylene glycol (meth)acrylate, ethoxy-polyethylene glycol (meth)acrylate, hydroxy-polyethylene glycol (meth)acrylate, methoxy-diethylene glycol (meth) acrylate, ethoxy-diethylene glycol (meth) acrylate, hydroxy-diethylene glycol (meth)acrylate, methoxy-triethylene glycol (meth)acrylate, ethoxy-triethylene glycol (meth)acrylate and hydroxy-triethylene glycol (meth)acrylate.

Examples of the phosphorylcholine (meth)acrylate include 2-(meth)acryloyloxyethyl phosphorylcholine.

The (meth)acrylic acids may be used alone or in combination of two or more. In this specification, the (meth)acrylic acid is a generic term for acrylic acid and methacrylic acid, and the (meth)acrylate is a generic term for acrylate and methacrylate.

The method for improving the degree of acetalization is not particularly limited, but adding an excess amount of the aldehyde in the acetalization reaction allows the acetalization reaction to proceed sufficiently.

In the present specification, the synthetic resin preferably has in a part thereof a Bronsted basic group. This is because, when a part of the synthetic resin is modified with a Bronsted basic group, in serum-free medium culture containing no feeder cell or adhesive protein, the initial fixation rate after cell seeding is improved and the cell culture becomes easier.

The Bronsted basic group is a generic term for a substituent that can receive a hydrogen ion $H^+$ from another substance. Examples of the Bronsted basic group include amine-based basic groups such as a substituent having an amine structure, a substituent having an imine structure, a substituent having an amide structure and a substituent having an imide structure.

Accordingly, as such a synthetic resin, synthetic resins are preferable containing as a structural unit at least one selected from the group consisting of a structural unit having an imine structure, a structural unit having an amine structure, a structural unit having an amide structure and a structural unit having an imide structure.

In the present invention, the imine structure refers to a structure having a C=N bond. The synthetic resin preferably has an imine structure on the side chain. In addition, the imine structure may be directly bonded to a carbon constituting the main chain of the synthetic resin, or may be bonded via a linking group such as an alkylene group. Note that having the imine structure on the side chain includes having the imine structure on the graft chain of the synthetic resin. Examples of the structural unit having an imine structure include a structural unit represented by the following formula (1).

[Chemical 1]

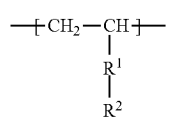
(1)

In the formula (1), $R^1$ represents a single bond or an alkylene group, and $R^2$ represents a group having an imine structure.

In the formula (1), when $R^1$ is an alkylene group, the preferred lower limit of the number of carbon atoms in the alkylene group is 1, and the preferred upper limit is 12. When the number of carbon atoms in the alkylene group exceeds 12, optimum strength may not be obtained. When $R^1$ is an alkylene group, the more preferred upper limit of the number of carbon atoms in the alkylene group is 5.

In the formula (1), when $R^1$ is an alkylene group, examples of the alkylene group includes linear alkylene groups such as a methylene group, ethylene group, trimethylene group, tetramethylene group, pentamethylene group, hexamethylene group, octamethylene group and decamethylene group, branched alkylene groups such as a methyl methylene group, methylethylene group, 1-methylpentylene group and 1,4-dimethylbutylene group, and cyclic alkylene groups such as a cyclopropylene group, cyclobutylene group and cyclohexylene group. Among them, a linear alkyl group such as a methylene group, ethylene group, trimethylene group and tetramethylene group is preferable, and a methylene group and ethylene group are more preferable.

The $R^2$ includes a functional group represented by the following formula (2).

[Chemical 2]

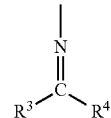
(2)

In the formula (2), $R^3$ represents a hydrogen atom or a hydrocarbon group having 1 to 18 carbon atoms, and $R^4$ represents a hydrocarbon group having 1 to 18 carbon atoms.

The hydrocarbon group includes a saturated hydrocarbon group, an unsaturated hydrocarbon group and an aromatic hydrocarbon group. The hydrocarbon group may be one composed of only any one of a saturated hydrocarbon group, an unsaturated hydrocarbon group and an aromatic hydrocarbon group, or one in which two or more of them are used.

Examples of the saturated hydrocarbon group include methyl, ethyl, n-propyl, isopropyl, n-butyl, iso-butyl, sec-butyl, tert-butyl, pentyl, hexyl, heptyl, 2-ethylhexyl, octyl, nonyl, decyl, undecyl, dodecyl, tridecyl, tetradecyl, pentadecyl and octadecyl groups. Among them, a methyl group, ethyl group, n-propyl group and n-butyl group are preferable.

Examples of the aromatic hydrocarbon group include a phenyl group, toluyl group, xylyl group, t-butylphenyl group and benzyl group.

In the synthetic resin, it is preferable that in the structural unit having an imine structure, $R^1$ is a single bond, $R^3$ is a hydrogen atom, a methyl group or an ethyl group, and $R^4$ is a methyl group, an ethyl group or a propyl group.

In the synthetic resin, the preferred lower limit of the content of the structural unit having an imine structure is 0.1 mol %, and the preferred upper limit is 20.0 mol %. When the content of the structural unit having an imine structure is 0.1 mol % or more, the viscosity stability over time becomes better. When the content of the structural unit having an imine structure is 20.0 mol % or less, the fixation of cells can be enhanced. The more preferred lower limit of the content of the structural unit having an imine structure is 1.0 mol %, and the more preferred upper limit is 15.0 mol %.

In the synthetic resin, when a modified polyvinyl acetal resin is used as the synthetic resin, the ratio between the content of the structural unit having an imine structure and the degree of acetalization described below (the content of the structural unit having an imine structure/degree of acetalization) is preferably 0.001 to 0.5. Within the above range, high strength and excellent adhesiveness can be achieved at the same time, and the durability after adhesion can be improved.

The synthetic resin preferably has a structural unit having an amine structure or a structural unit having an amide structure.

The synthetic resin preferably has the amine structure or the amide structure on the side chain. In addition, the amine structure or the amide structure may be directly bonded to a carbon constituting the main chain of the synthetic resin, or may be bonded via a linking group such as an alkylene group. Furthermore, the amine structure may be a primary amine, a secondary amine, a tertiary amine or a quaternary amine. Among them, a primary amine is preferable from the viewpoint of the fixation of cells.

Note that having the amine structure or amide structure on the side chain means having the amine structure or the amide structure on the graft chain of the synthetic resin.

In particular, the amine structure is preferably —$NH_2$. In the present invention, the amide structure refers to a structure having —C(=O)—NH—. In particular, the structural unit having the amine structure preferably is a structure represented by the following formula (3). In addition, the structural unit having the amide structure preferably has a structure represented by the following formula (4).

[Chemical 3]

(3)

[Chemical 4]

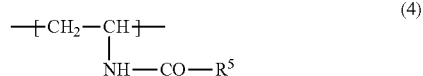
(4)

In the formula (4), $R^5$ represents a hydrogen atom or a hydrocarbon group having 1 to 10 carbon atoms. The hydrocarbon group includes an alkyl group, an alkenyl group, a cycloalkyl group and a cycloalkenyl group.

The preferred lower limit of the content of the structural unit having an amine structure or an amide structure is 0.1 mol %, and the preferred upper limit is 20 mol %. When the content of the structural unit having an amine structure or an amide structure is 0.1 mol % or more, additional properties can be made sufficient. When the content is 20 mol % or less, the solubility is not so excessively increased that the modified polyvinyl acetal resin powder can be easily taken out by precipitation method. The more preferred lower limit of the content is 0.5 mol %, and the more preferred upper limit is 10 mol %. The content of the structural unit having an amine structure or an amide structure can be measured by NMR or the like. In addition, the preferred lower limit of the total content of the structural unit having an amine structure or an amide structure and the structural unit having an imine structure is 0.1 mol %, and the preferable upper limit is 20 mol %. The more preferred lower limit of the content is 0.5 mol %, and the more preferred upper limit is 10 mol %.

In the synthetic resin, when both of the imine structure and the amine structure or the amide structure are contained, the ratio between the content of the structural unit having an imine structure and that of the structural unit having an amine structure or an amide structure (the structural unit having an imine structure/the structural unit having an amino group or an amide structure) is preferably 0.5/99.5 to 99.5/0.5. When the ratio is 0.5/99.5 or more, the viscosity stability over time can be sufficient, whereas when the above ratio is 99.5/0.5 or less, the crosslinking performance can be sufficiently exhibited from the viewpoint of the fixation of cells. The more preferred lower limit of the ratio is 5/95, and the more preferred upper limit is 75/25.

When a polyvinyl acetal resin is used as the synthetic resin, the degree of acetalization of the polyvinyl acetal resin (degree of butyralization in the case of the polyvinyl butyral resin) is not particularly limited, but is preferably 54 mol % or more, more preferably 60 mol % or more, still more preferably 65 mol % or more, and preferably 90 mol % or less, more preferably 85 mol % or less. When the degree of acetalization is equal to or higher than the above-mentioned lower limit, the fixation of cells is excellent, and thus cell proliferation can be performed with high efficiency. When the degree of acetalization is equal to or lower than the above-mentioned upper limit, the solubility in solvent can be better. The degree of acetal of the synthetic resin can be measured by NMR or the like.

When a polyvinyl acetal resin is used as the synthetic resin, the amount of acetyl group in the polyvinyl acetal resin is not particularly limited, but the lower limit is preferably 0.0001 mol %, and the upper limit is preferably 5 mol %.

The synthetic resin preferably includes at least one selected from the group consisting of a structural unit having an amine structure, a structural unit having an imine structure and a structural unit having an amide structure.

The synthetic resin preferably includes both of a structural unit having an imine structure and a structural unit having an amine structure.

Examples of the method for producing the modified polyvinyl acetal resin include a method for acetalizing using a conventionally known method a polyvinyl alcohol obtained by saponifying polyvinyl acetate obtained by copolymerizing the monomer having an imine structure with vinyl acetate. In addition, a method may also be used for introducing an imine structure by acetalizing using a conventionally known method a polyvinyl alcohol having a structural unit having an amino group or an amide structure. A method may also be used for acetalizing using a conventionally known method a modified polyvinyl alcohol having an imine structure obtained by post-modifying a polyvinyl alcohol having a structural unit having an amino group or an amide structure. Furthermore, an imine structure may be introduced by post-modifying an unmodified polyvinyl acetal resin. In other words, the modified polyvinyl acetal resin may be an acetalized product of a polyvinyl alcohol having a structural unit having an amino group or an amide structure. Among them, a method is preferable for producing a modified polyvinyl acetal resin having an imine structure by acetalizing a polyvinyl alcohol having a structural unit having an amino group or an amide structure. In particular, when such a method is used, an imine structure can be obtained by adding excessive amounts of aldehyde and acid catalyst for use in acetalization.

In the method for excessively adding aldehyde, it is preferable to add 70 to 150 parts by weight aldehyde to 100 parts by weight a polyvinyl alcohol having a structural unit having an amino group or an amide structure. Particularly, as the aldehyde, acetaldehyde, propionaldehyde, n-butyraldehyde, isobutyraldehyde, n-valeraldehyde and phenylaldehyde are preferable.

In the method for excessively adding an acid catalyst, it is preferable to add the acid catalyst in an amount of 0.5% by weight or more with respect to the whole weight. In addition, it is preferable to add 5.0 to 70.0 parts by weight acid catalyst to 100 parts by weight a polyvinyl alcohol having a structural unit having an amino group or an amide structure. Particularly, as the acid catalyst, hydrochloric acid, nitric acid, sulfuric acid and para-toluenesulfonic acid are preferable.

The acetalization can be performed using a known method, and is preferably performed in an aqueous solvent, a mixed solvent of water and an organic solvent having compatibility with water, or an organic solvent. As the organic solvent compatible with water, for example, an alcohol-based organic solvent can be used. Examples of the organic solvent include alcohol-based organic solvents, aromatic organic solvents, aliphatic ester-based solvents, ketone-based solvents, lower paraffin-based solvents, ether-based solvents and amine-based solvents. Examples of the alcohol-based organic solvent include methanol, ethanol, n-propanol, isopropanol, n-butanol and tert-butanol. Examples of the aromatic organic solvent include xylene, toluene, ethylbenzene and methyl benzoate.

Examples of the aliphatic ester-based solvent include methyl acetate, ethyl acetate, butyl acetate, methyl propionate, ethyl propionate, methyl butyrate, ethyl butyrate, methyl acetoacetate and ethyl acetoacetate.

Examples of the ketone-based solvent include acetone, methyl ethyl ketone, methyl isobutyl ketone, cyclohexanone, methylcyclohexanone, benzophenone and acetophenone. The lower paraffin-based solvents include hexane, pentane, octane, cyclohexane and decane. The ether-based solvents include diethyl ether, tetrahydrofuran, ethylene glycol dimethyl ether, ethylene glycol diethyl ether and propylene glycol diethyl ether. The amide-based solvents include N,N-dimethylformamide, N,N-dimethylacetamide, N-methylpyrrolidone and acetanilide.

The amine-based solvents include ammonia, trimethylamine, triethylamine, n-butylamine, di-n-butylamine, tri-n-butylamine, aniline, N-methylaniline, N,N-dimethylaniline and pyridine.

These can be used alone or as a mixture of two or more solvents. Among them, ethanol, n-propanol, isopropanol and tetrahydrofuran are particularly preferable from the viewpoints of solubility in a resin and simplicity during purification.

The acetalization is preferably performed in the presence of an acid catalyst. The acid catalyst is not particularly limited, but includes mineral acids such as sulfuric acid, hydrochloric acid, nitric acid and phosphoric acid, carboxylic acids such as formic acid, acetic acid and propionic acid, and sulfonic acids such as methanesulfonic acid, ethanesulfonic acid, benzenesulfonic acid and para-toluenesulfonic acid. These acid catalysts may be used alone or in combination of two or more compounds. Among them, hydrochloric acid, nitric acid and sulfuric acid are preferable, and hydrochloric acid is particularly preferable.

The polyvinyl acetal resin may be a graft copolymer with the vinyl compound. The vinyl compound includes ethylene, allylamine, vinylpyrrolidone, maleic anhydride, maleimide, itaconic acid and (meth)acrylic acids.

The graft copolymer contains a graft copolymer having a "unit composed of polyvinyl acetal" and a "unit composed of a vinyl compound" (hereinafter, also simply referred to as "graft copolymer"). The vinyl compound refers to a compound having a structural unit having an ethenyl group ($H_2C=CH-$).

In the present invention, the "unit composed of polyvinyl acetal" and the "unit composed of a vinyl compound" refer to "polyvinyl acetal" and a "unit composed of a vinyl compound" present in the graft copolymer. In addition, a graft copolymer having a unit composed of a unit composed of polyvinyl acetal and a unit composed of a vinyl compound refers to a branched copolymer in which, to a "unit composed of polyvinyl acetal" or a "unit composed of a vinyl compound" composing the main chain, a "unit composed of polyvinyl acetal" or a "unit composed of a vinyl compound" composing a side chain different from the main chain is bonded.

The molecular weight of the graft copolymer is not particularly limited, but it is preferable that the number average molecular weight (Mn) be 10,000 to 600,000, the weight average molecular weight (Mw) be 20,000 to 1,200,000 and the ratio (Mw/Mn) be 2.0 to 40. When the Mn, Mw and Mw/Mn are in such ranges, the strength of the scaffolding material for cell is suitably maintained.

The method for measuring the degree of acetalization in the graft copolymer include a method for measuring the degree of acetalization by $^1$H-NMR measurement in which a soluble component in xylene is dissolved in deuterated dimethyl sulfoxide.

The polyvinyl acetal resin preferably contains at least one structural unit selected from the group consisting of a structural unit having an imine structure, a structural unit having an amine structure and a structural unit having an amide structure in an amount of 0.1 to 30 mol %. From the viewpoint of the cell adhesion immediately after seeding, it is more preferable to contain 1 to 10 mol %.

Examples of the method for confirming the content of a structural unit having an amine structure, a structural unit having an amide structure or a structural unit having an imine structure include a confirming method by $^1$H-NMR.

When a polyvinyl acetal resin is used as the synthetic resin, the lower limit of the average degree of polymerization of the polyvinyl acetal resin is preferably 100, more preferably 200, still more preferably 500, even more preferably 1,500. When the average degree of polymerization is in the above range, the strength of the scaffolding material can be suitably maintained even when swelled in a medium to be used for cell culture, so that the cell proliferation is improved. The upper limit of the average degree of polymerization is preferably 6000, more preferably 3000, still more preferably 2500. When the average degree of polymerization is in the above range, the handleability is good and the scaffolding material can be suitably molded.

Other Details of Scaffolding Material for Cell Culture

The scaffolding material for cell culture according to the present invention is used for culturing cells. The scaffolding material for cell culture according to the present invention is used as a scaffold for cells when the cells are cultured. In the scaffolding material for cell culture according to the present invention, it is particularly preferable that a cell mass be seeded. However, in the scaffolding material for cell culture according to the present invention, a cell mass may not be seeded.

The cells include animal cells such as human, mouse, rat, pig, bovine and monkey cells. In addition, the cells include somatic cells, such as stem cells, progenitor cells and mature cells. The somatic cell may also be cancer cells.

The mature cells include nerve cells, cardiomyocytes, retinal cells and hepatocytes.

The stem cells include mesenchymal stem cells (MSCs), iPS cells, ES cells, Muse cells, embryonal cancer cells, embryonic germ stem cells and mGS cells.

Cell Culture Method

According to the scaffolding material for cell culture, various cells can be cultured. The cells include the above described cells. This is because the scaffolding material for cell culture according to the present invention is hardly swelled with the water in a culture medium, and thus can maintain so suitable hydrophilicity and strength that the fixation rate of cells after seeding is improved.

The cell culture method preferably includes a step of seeding a cell mass on the scaffolding material for cell culture. The cell mass can be obtained by adding a cell detaching agent to a confluent culture container and uniformly performing crushing by pipetting. The cell detaching agent is not particularly limited, but is preferably an ethylenediamine/phosphate buffer solution. The size of the cell mass is preferably 50 μm to 200 μm.

Container for Cell Culture

The present invention also relates to a container for cell culture in which the scaffolding material for cell culture is used. In other words, the present invention relates to a container for cell culture, wherein the container for cell culture includes a resin film composed of the cell scaffolding material on at least a part of a cell culture region. In the container for cell culture, the scaffolding material for cell culture is preferably in the form of a film, and is preferably a resin film. The container for cell culture includes a container body and the scaffolding material for cell culture (resin film) arranged on the surface of the container body.

Figure 1B:
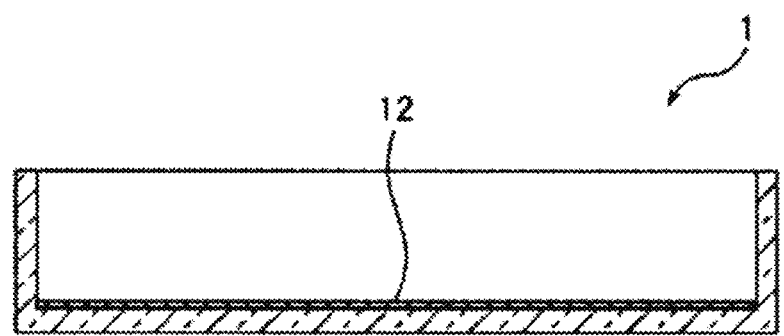
FIG. 1B is a schematic sectional side view thereof.

FIG. 1A is a schematic perspective view of the container for cell culture according to an embodiment, and FIG. 1B is a schematic sectional side view thereof. The container for cell culture is not particularly limited for shape, but examples thereof include an aspect in which a bottomed cylindrical Petri dish 1 as shown in FIG. 1A is prepared, and a resin film 12 is provided on a cell culture region on the bottom surface as shown in FIG. 1B.

In cell culture, the scaffolding material for cell culture can be used not only for planar culture (two-dimensional culture method) but also for culturing cells on a base material in a state closer to an in-vivo state, such as a porous membrane or a hydrogel (three-dimensional culture method). This is because cells can be efficiently proliferated by using the scaffolding material for cell culture in a bioreactor or the like.

The scaffolding material for cell culture is preferably used in a two-dimensional culture method because it has suitable hydrophilicity and strength.

The container for planar culture (two-dimensional culture method) is not particularly limited for shape and size, but includes a test plate for cell culture having one or more wells (holes) and a flask for cell culture. For example, a container for cell culture having six wells as shown in FIG. 2 can be used. The number of wells in the microplate is not limited, but includes, for example, 2, 4, 6, 12, 24, 48, 96 and 384.

The shape of the well is not particularly limited, but includes, for example, a perfect circle, ellipse, triangle, square, rectangle, and pentagon. The shape of the bottom surface of the well is not particularly limited, but includes a flat bottom, a round bottom and irregularities.

The material of the test plate for cell culture having one or more wells (holes) or the material of the flask for cell culture are not particularly limited, but includes a polymer resin, metal and inorganic material. The polymer resin includes polystyrene, polyethylene, polypropylene, polycarbonate, polyester, polyisoprene, cycloolefin polymer, polyimide, polyamide, polyamideimide, (meth)acrylic resin, epoxy resin and silicone. The metal includes stainless steel, copper, iron, nickel, aluminum, titanium, gold, silver and platinum. The inorganic material includes silicon oxide (glass), aluminum oxide, titanium oxide, zirconium oxide, iron oxide and silicon nitride.

In addition to the above, the scaffolding material for cell culture can be used in a suspension culture method in which cells are freely suspended and grown in a medium.

Other Embodiments

In addition to the scaffolding material for cell culture, the present invention provides an invention using the scaffolding material for cell culture as another embodiment.

For example, in the present invention, a carrier (medium) for cell culture containing the scaffolding material for cell culture and a polysaccharide is provided. Various polysaccharides can be used as the polysaccharide without any particular limitation. Among them, water-soluble polysaccharides are preferable.

In addition, the present invention provides a fiber for cell culture containing the scaffolding material for cell culture. In this case, it is preferable that the scaffolding material for cell culture be applied on the fiber. In addition, the scaffolding material for cell culture may be in a form impregnated or kneaded in the fiber. The fiber for cell culture is suitable for a three-dimensional culture method for cells that are difficult to adhere to a planar structure such as a flask, but easily adhere to a three-dimensional structure such as a fibril-like structure.

The scaffolding material for cell culture may be crosslinked. This is because crosslinking can suppress water swelling and suitably increase the strength. Using a crosslinking agent can provide the crosslinked scaffolding material for cell culture.

The crosslinking agent is not particularly limited, but includes polyalcohol, polycarboxylic acid, hydroxycarboxylic acid, metal soap and polysaccharides.

The polyalcohol is not particularly limited, but includes ethylene glycol, propylene glycol, butanediol, pentanediol, hexanediol, heptanediol, octanediol, nonanediol, decanediol, dodecanediol, undecanediol, diethylene glycol, triethylene glycol, tetraethylene glycol, polyethylene glycol, catechol, pyrogallol, diboronic acid, methylenediboronic acid, ethylenediboronic acid, propylene diboronic acid, phenylenediboronic acid, biphenyldiboronic acid and bisphenol derivatives.

The polycarboxylic acid is not particularly limited, but includes oxalic acid, malonic acid, succinic acid, glutaric acid, adipic acid, pimelic acid, suberic acid, azelaic acid, sebacic acid, phthalic acid and poly(meth)acrylic acid.

The hydroxycarboxylic acid is not particularly limited, but includes glycolic acid, lactic acid, tartronic acid, glyceric acid, hydroxybutyric acid, malic acid, tartaric acid, cytomaric acid, citric acid, isocitric acid, leucic acid, mevalonic acid, pantoic acid, ricinoleic acid, ricineraidic acid, cerebronic acid, quinic acid, shikimic acid, hydroxybenzoic acid, salicylic acid, creosoteic acid, vanillic acid, syringic acid, pyrocatechuic acid, resorcylic acid, protocatechuic acid, gentisic acid, orsellinic acid, gallic acid, mandelic acid, benzilic acid, atrolactic acid, melilotic acid, phloretic acid, coumaric acid, umbellic acid, caffeic acid, ferulic acid, sinapinic acid and hydroxystearic acid.

The metal soap is not particularly limited, but includes salts of fatty acids such as stearic acid, lauric acid, ricinoleic acid and octylic acid with metals such as lithium, sodium, magnesium, calcium, barium, zinc and aluminum.

The polysaccharides are not particularly limited, but include pectin, guar gum, xanthan gum, tamarind gum, carrageenan, propylene glycol, carboxymethylcellulose, amylose, amylopectin, glycogen, cellulose, chitin, agarose, carrageenan, heparin, hyaluronic acid, xyloglucan and glucomannanic acid.

EXAMPLES

Hereinafter, a description is made of the present invention with reference to Examples and Comparative Examples, but the present invention is not limited to the following Examples. The content of the structural unit having an amine structure (mol %), content of the structural unit having an imine structure (mol %), content of the structural unit having an amide structure (mol %), degree of acetalization (mol %), amount of acetyl group (mol %) and amount of hydroxyl group (mol %) in an obtained synthetic resin were measured by dissolving the synthetic resin in DMSO-d6 (dimethyl sulfoxide) and using $^1$H-NMR (nuclear magnetic resonance spectrum).

Example 1

Preparation of Polyvinyl Butyral

A reactor equipped with a stirrer was charged with 2,700 mL of ion-exchanged water, 300 g of polyvinyl alcohol containing 2 mol % structural unit having an amino group represented by the formula (3) (having an average degree of polymerization of 250 and a degree of saponification of 97 mol %), followed by dissolution by heating with stirring to prepare a solution. Next, to the solution, 35% by mass hydrochloric acid as a catalyst was added such that the concentration of hydrochloric acid became 0.2% by mass, and after the temperature was adjusted to 15° C., 22 g of n-butyraldehyde (n-BA) was added while being stirred. Thereafter, when 148 g of n-butyraldehyde (n-BA) was added, polyvinyl butyral was precipitated in the form of white particles. Fifteen minutes after the precipitation, 35% by mass hydrochloric acid was added such that the concentration of hydrochloric acid became 1.8% by mass, and the mixture was heated to 550° C., and then aged at 50° C. for 2 hours. Next, the solution was cooled and neutralized, and then the polyvinyl butyral was washed with water and dried.

The obtained polyvinyl butyral had an average degree of polymerization of 250, an amount of hydroxyl group of 20 mol %, an amount of acetyl group of 1 mol % and a degree of acetalization of 77 mol %.

The elemental composition of the obtained resin was analyzed by X-ray photoelectron spectroscopy (apparatus: multifunctional scanning X-ray photoelectron spectrometer (XPS), PHI 5000 VersaProbe III, manufactured by ULVAC-PHI, Inc.). Then, the total amount of all the detected elements was defined as 100%, and the occupation rate (%) of nitrogen in all the elements was defined as the nitrogen content.

Preparation of Container for Cell Culture

By dissolving 1 g of the obtained polyvinyl butyral resin in 19 g of butanol, a solution of polyvinyl butyral resin was obtained. By discharging 150 µL of the obtained solution of polyvinyl butyral resin onto a φ22 mm cover glass (manufactured by Matsunami Glass Ind., Ltd., 22 round No. 1 was used after dust was removed with air duster) and spinning it at 2,000 rpm for 20 seconds using a spin coater, a smooth resin film was obtained. By placing the obtained resin film on a φ22 mm polystyrene dish together with the cover glass, a container for cell culture was obtained.

Using the obtained container for cell culture, tests were conducted under the following conditions.

Method for Cell Culture Test (iPS Cells)

To the obtained container for cell culture, 1 mL of phosphate buffered saline was added, and the mixture was allowed to stand for 1 hour in an incubator at 37° C. After removing the phosphate buffered saline in the dish, $1.5 \times 10^4$ h-iPS cells 253G1 were seeded for performing culture in the presence of 1 mL of medium TeSR E8 (manufactured by STEM CELL) and 10 µM of ROCK-Inhibitor (Y27632) in an incubator at 37° C. under a $CO_2$ concentration of 5%. Every 24 hours, the medium was exchanged by removing 750 µL of medium, and adding 250 µL of new TeSR E8 such that the ROCK-Inhibitor (Y27632) was adjusted to be at 10 µM.

Method for Cell Mass Culture Test (iPS Cells)

To the obtained container for cell culture, 1 mL of phosphate buffered saline was added, and the mixture was allowed to stand for 1 hour in an incubator at 37° C. Thereafter, the phosphate buffered saline in the culture container was removed. A confluent colony of h-iPS cells 252G1 was added to a 35 mm dish, and then 1 mL of 0.5 mM ethylenediamine/phosphate buffer solution was added, followed by standing at room temperature for 2 minutes. Thereafter, the ethylenediamine/phosphate buffer solution was removed, $1.0 \times 10^5$ cell mass crushed to 50 to 200 µm by pipetting with 1 mL of TeSR E8 medium was seeded in the culture container for performing culture in the presence of 1 mL of medium TeSR E8 (manufactured by STEM CELL) and 10 µM of ROCK-Inhibitor (Y27632) in an incubator at 37° C. under a $CO_2$ concentration of 5%. Every 24 hours, the medium was exchanged by removing 750 µL of the medium and adding 250 µL of new TeSR E8.

Method for Evaluating Culture (iPS Cell)

(1) Initial Adhesion (iPS Cells)

Figure 3:
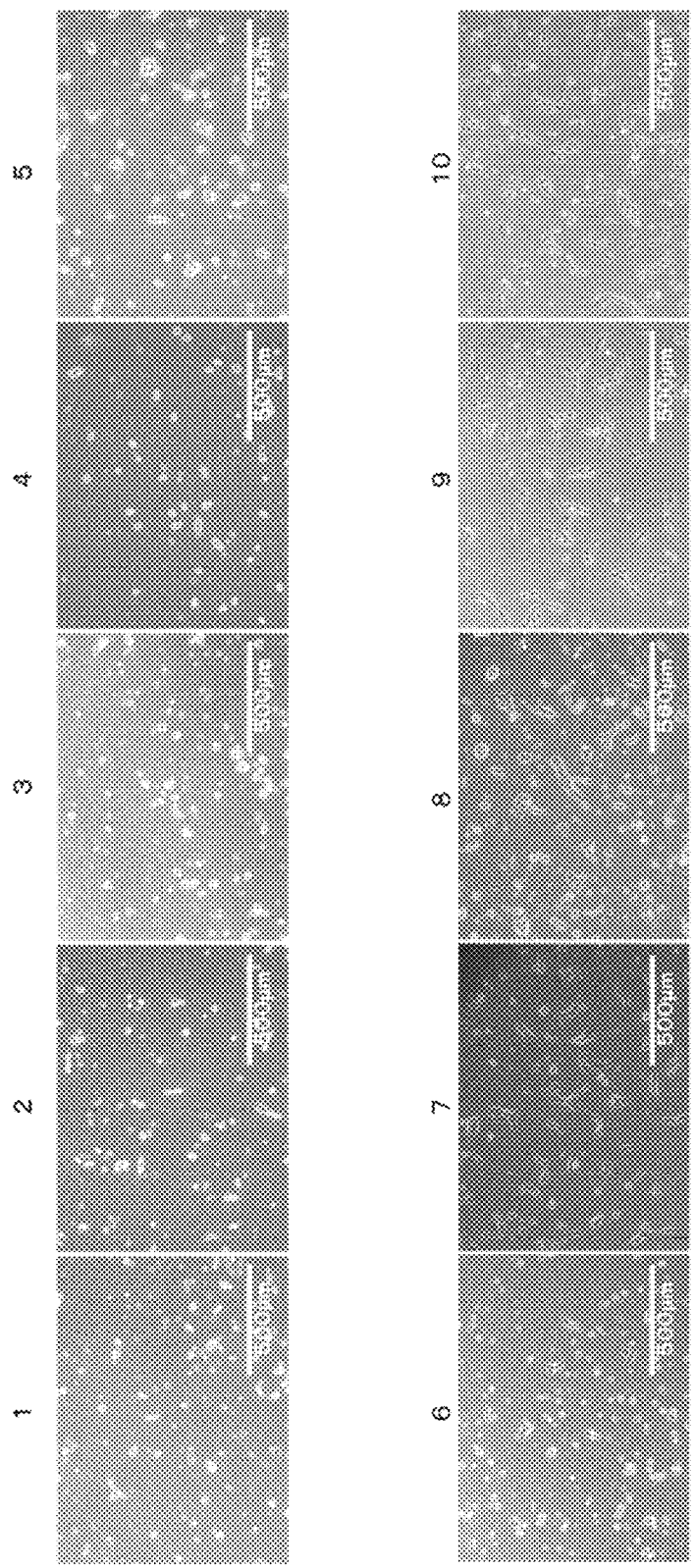
FIG. 3 is a view showing evaluation criteria for initial adhesion 24 hours after cell seeding.
Figure 4A:
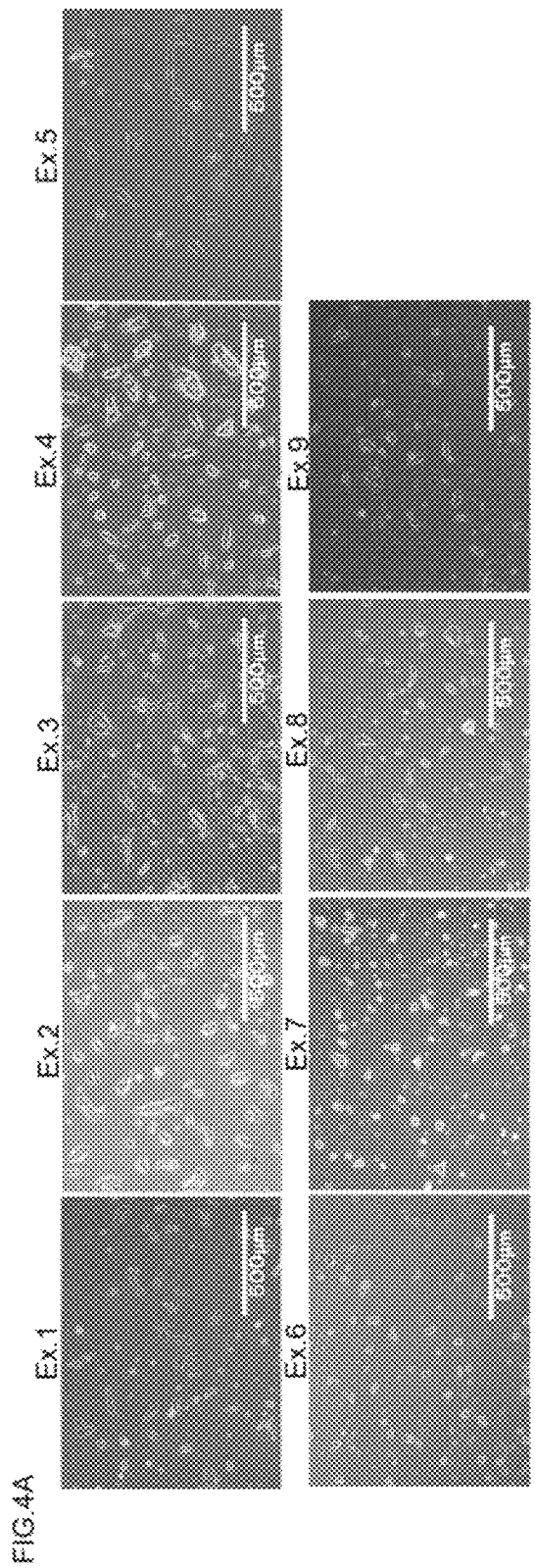
FIG. 4A and FIG. 4B are each phase contrast micrographs 24 hours after iPS cell seeding according to Examples and Comparative Examples.
Figure 4B:
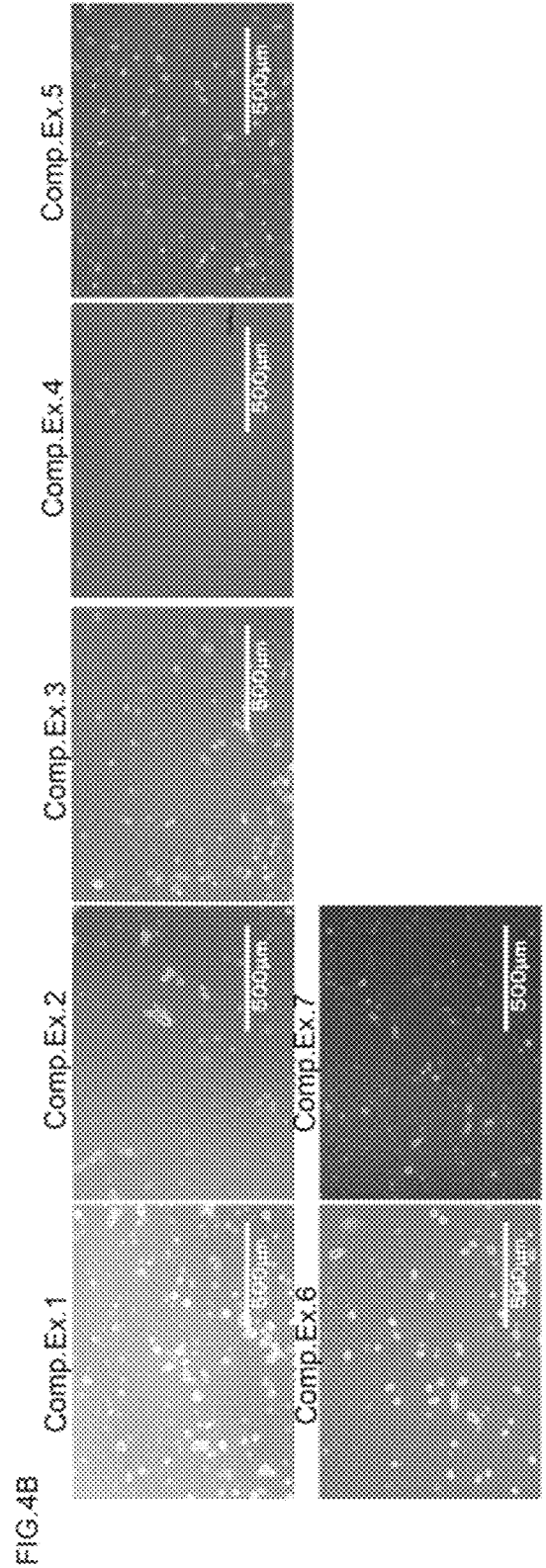

In the cell culture test for iPS cells, a cell image 24 hours after the cell seeding was obtained using a phase-contrast microscope (manufactured by Olympus Corporation, IX73) at a magnification of 10×10. At that time, an image of a visual field showing the most average form of adhesion in the culture container was obtained. The obtained images were compared with Samples 1 to 10 in FIG. 3 to evaluate the initial adhesion in consideration of the number of adherent cells and the morphology of adherent cells. In FIG. 3, it is shown that the number of cells increases from Samples 1 to 8 in this order. In addition, it is shown that the pseudopodia of the cells elongate and the cells are in a better adhesion state, from Samples 8 to 10 in this order. The obtained results for Examples and Comparative Examples are summarized in FIGS. 4A and 4B.

(2) Cell Proliferation (iPS Cells)

Figure 5:
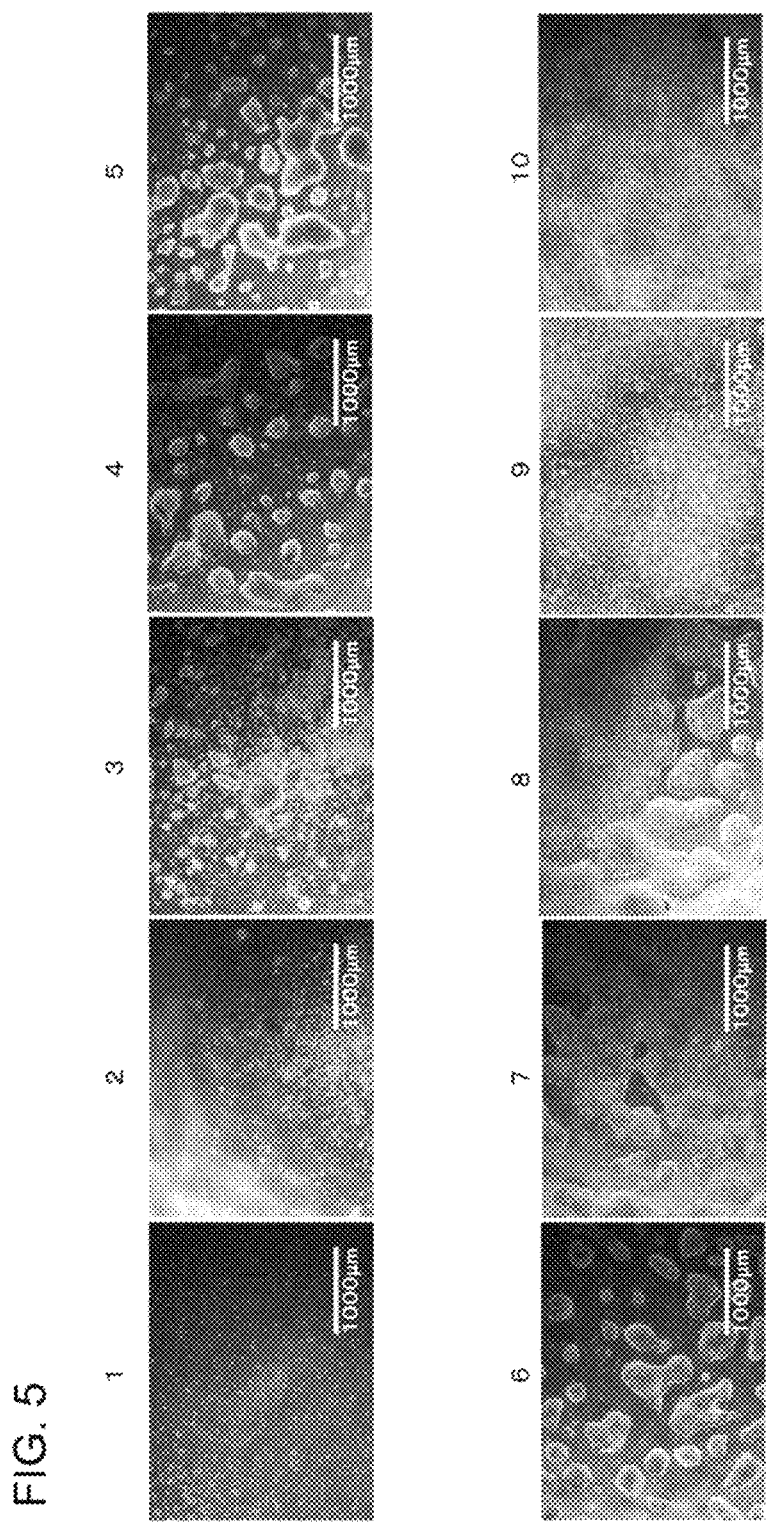
FIG. 5 is a view showing evaluation criteria for cell proliferation 5 days after cell seeding.
Figure 6A:
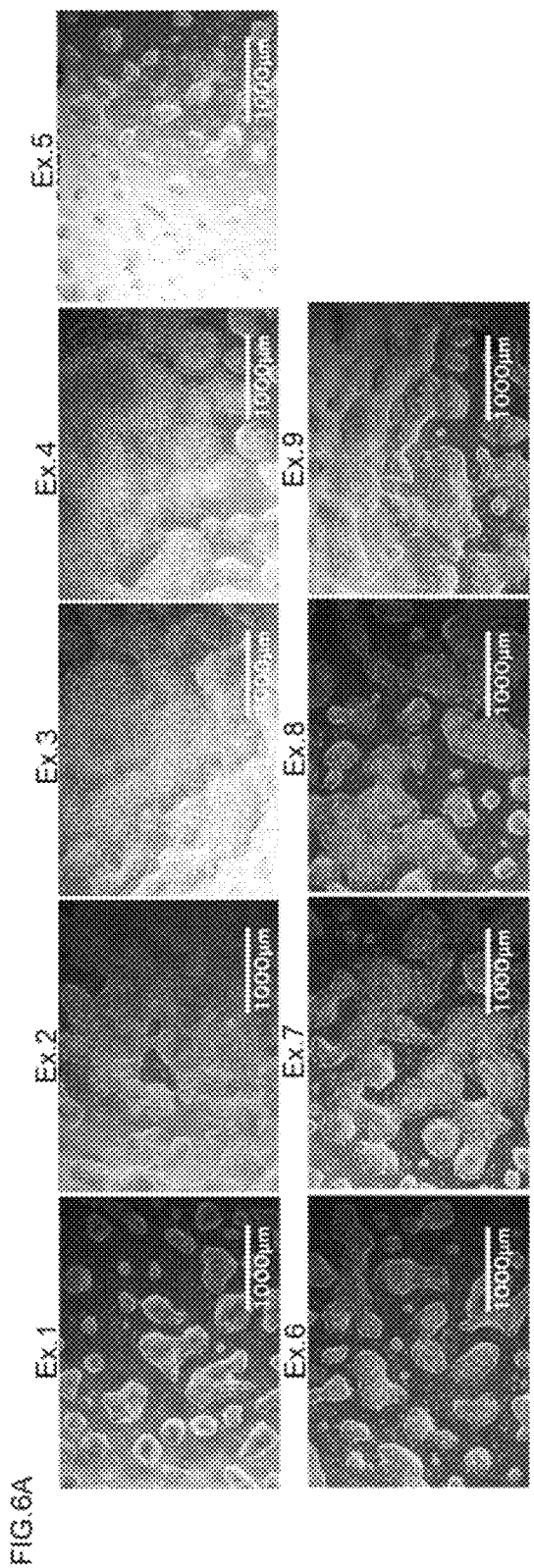
FIG. 6A and FIG. 6B are each phase contrast micrographs 5 days after iPS cell seeding according to Examples and Comparative Examples.
Figure 6B:
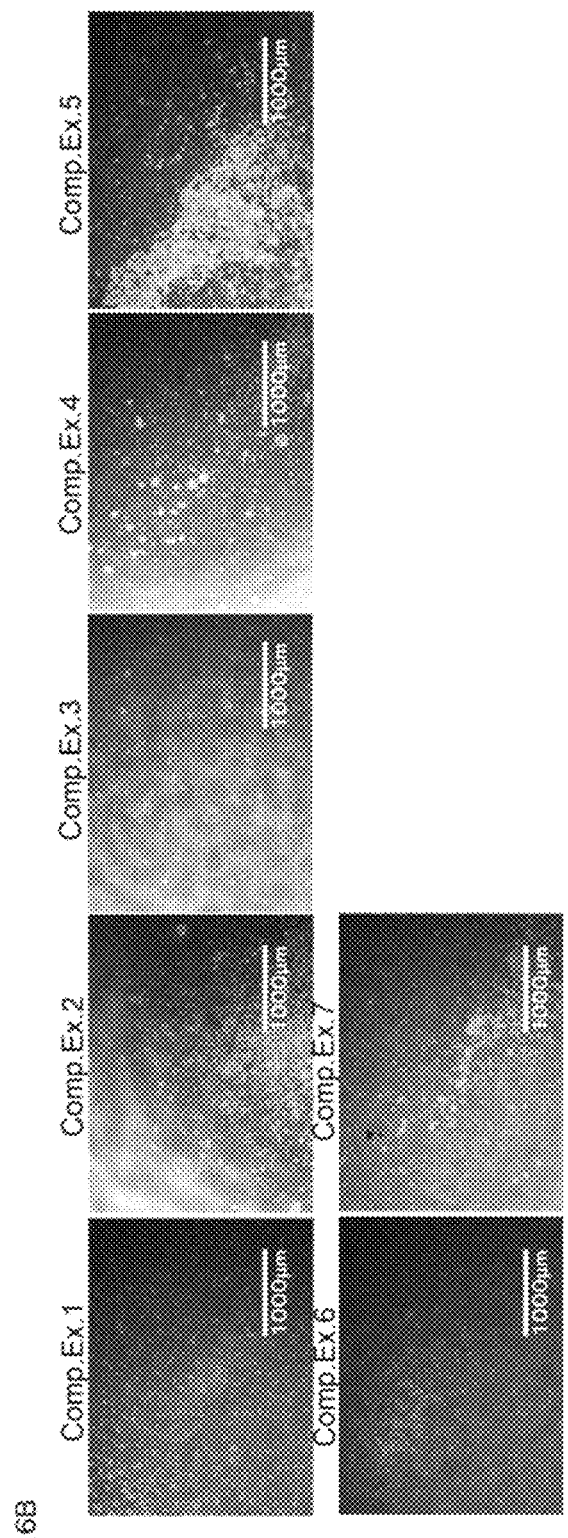

In the cell culture test for iPS cells, a cell image 5 days after the cell seeding was obtained using a phase-contrast microscope (manufactured by Olympus Corporation, IX73) at a magnification of 10×4. At that time, an image of a visual field showing the most average form of adhesion in the culture container was obtained. The cell proliferation was evaluated by comparing the obtained image with Samples 1 to 10 in FIG. 5. In FIG. 5, a higher evaluation was obtained as the colony grew due to cell proliferation. When the colony grows too much in the lateral direction (the vertical and horizontal direction in the view), it starts to pile up in the vertical direction (the direction toward the front side of the view), so that light transmittance tends to decrease. The obtained results for Examples and Comparative Examples are summarized in FIGS. 6A and 6B.

(3) Adhesion Maintenance (iPS Cells)

In the cell mass culture test for iPS cells, the time during which the cell mass could maintain adhesion was evaluated according to the following criteria.
0: All cells were detached in less than 30 minutes after medium exchange.
1: Adhesion was maintained for 30 minutes or more after medium exchange, but all cells were detached in less than 1 hour.
2: Adhesion was maintained for 1 hour or more after medium exchange, but all cells detached in less than 24 hours.
3: Adhesion was maintained for 24 hours or more after medium exchange.
The obtained cell mass was confirmed to maintain undifferentiation by alkaline phosphatase (ALP) staining test.

Method for Cell Culture Test (Hepatocytes)

To the obtained container for cell culture, 1 mL of phosphate buffered saline was added, and the mixture was allowed to stand for 1 hour in an incubator at 37° C. After removing the phosphate buffered saline in the dish, $3\times10^4$ cells of human fresh hepatocytes derived from a chimeric mouse (PXB-cells manufactured by PhoenixBio Co., Ltd.) were seeded. Next, 1 mL of medium RM-101 (manufactured by Toyo Gosei Co., Ltd.) was added, followed by culture in an incubator at 37° C. with a $CO_2$ concentration of 5%.

Method for Evaluating Hepatocyte Culture (4) Initial Adhesion (Fixation After Seeding) (Hepatocytes)

In the cell culture test for hepatocytes, cells were detached using trypsin 24 hours after seeding of the cells. The number of cells was measured using an auto cell counter (Auto Cell Counter EVE, manufactured by NanoEnteck Inc.).

Evaluation Criteria for Initial Adhesion (Hepatocytes)

∘∘∘: The number of cells is $2.5\times10^4$ cells or more
∘∘: The number of cells is $1.5\times10^4$ cells or more and less than $2.5\times10^4$ cells
∘: The number of cells is $1.0\times10^4$ cells or more and less than $1.5\times10^4$ cells
×: The number of cells is less than $1.0\times10^4$ cells (5) Cell Proliferation (Hepatocytes)

In the cell culture test for hepatocytes, cells were detached using trypsin 3 days after seeding of the cells. The number of cells was measured using an auto cell counter (Auto Cell Counter EVE, manufactured by NanoEnteck Inc.).

Evaluation Criteria for Cell Proliferation (Hepatocytes)

∘∘∘: The number of cells is $2.0\times10^5$ cells or more
∘∘: The number of cells is $1.0\times10^5$ cells or more and less than $2.0\times10^5$ cells
∘: The number of cells is $5.0\times10^4$ cells or more and less than $1.0\times10^5$ cells
×: The number of cells is less than $5.0\times10^4$ cells Example 2

The test was performed in the same manner as in Example 1 except that a polyvinyl alcohol containing 2 mol % structural unit having an amino group represented by the formula (3) having an average degree of polymerization of 1,600 and a degree of saponification of 97 mol % was used, instead of the polyvinyl alcohol containing 2 mol % structural unit having an amino group represented by the formula (3) (having an average degree of polymerization of 250 and a degree of saponification of 97 mol %).

Example 3

A polyvinyl acetal was obtained in the same manner as in Example 1 except that a polyvinyl alcohol having an average degree of polymerization of 250 and a degree of saponification of 97 mol % was used, instead of the polyvinyl alcohol containing 2 mol % structural unit having an amino group represented by the formula (3) (having an average degree of polymerization of 250 and a degree of saponification of 97 mol %). In 500 parts by weight tetrahydrofuran, 100 parts by weight obtained polyvinyl acetal having a degree of polymerization of about 250 and 1 part by weight N-vinylpyrrolidone were dissolved to prepare a resin solution. In the prepared resin solution, 0.05 parts by weight Irgacure184 (manufactured by BASF) was dissolved, and the resultant mixture was applied onto a PET film. The coated product was irradiated with light having a wavelength of 365 nm at an integrated light amount of 2000 mJ/cm$^2$ using a UV conveyor device "ECS301G1" manufactured by Eye Graphics Co., Ltd. at 25° C. to prepare a composite resin solution. The prepared composite resin solution was vacuum-dried at 80° C. for 3 hours to prepare a composite resin. The prepared resin was measured for weight average molecular weight in terms of polystyrene by GPC method using "2690 Separations Model" manufactured by Waters Corporation as a column. The weight average molecular weight was about 40,000. The prepared composite resin was adjusted to a 3% by weight butanol solution, and the test was conducted in the same manner as in Example 1.

Example 4

The test was performed in the same manner as in Example 3 except that 10 parts by weight N-vinylpyrrolidone was added to 100 parts by weight polyvinyl acetal. The weight average molecular weight of the obtained resin was about 60,000.

Example 5

The test was performed in the same manner as in Example 3 except that 30 parts by weight N-vinylpyrrolidone was added to 100 parts by weight polyvinyl acetal. The weight average molecular weight of the obtained resin was about 50,000.

Example 6

The test was performed in the same manner as in Example 3 except that 2 parts by weight N-isopropylacrylamide was added to 100 parts by weight polyvinyl acetal. The weight average molecular weight of the obtained resin was about 60,000.

Example 7

The test was performed in the same manner as in Example 3 except that 2 parts by weight polyamide was added to 100 parts by weight polyvinyl acetal. The weight average molecular weight of the obtained resin was about 60,000.

Example 8

The test was performed in the same manner as in Example 3 except that 2 parts by weight poly-L-lysine was added to 100 parts by weight polyvinyl acetal. The weight average molecular weight of the obtained resin was about 50,000.

Example 9

In 300 parts by weight tetrahydrofuran, 5 parts by weight N-vinylpyrrolidone, 15 parts by weight butyl methacrylate, 30 parts by weight ethyl acrylate and 50 parts by weight methyl methacrylate were dissolved to prepare an acrylic monomer solution. In the prepared acrylic monomer solution, 2 parts by weight Irgacure184 (manufactured by BASF) was dissolved, and the resultant mixture was applied onto a PET fill. The coated product was irradiated with light having a wavelength of 365 nm at an integrated light amount of 2,000 mJ/cm$^2$ using a UV conveyor device "ECS301G1" manufactured by Eye Graphics Co., Ltd. at 25° C. to prepare an acrylic resin solution. The prepared acrylic resin solution was vacuum-dried at 80° C. for 3 hours to prepare an acrylic resin. The prepared acrylic resin was adjusted to a 3% by weight butanol solution, and the test was conducted in the same manner as in Example 1. The weight average molecular weight of the obtained resin was about 90,000.

Comparative Example 1

The test was performed in the same manner as in Example 1 using only a polystyrene dish without using the scaffolding material resin.

Comparative Example 2

The test was performed in the same manner as in Example 1 except that the addition amounts of n-butyraldehyde was changed to 22 g and 88 g instead of 22 g and 148 g in Example 1.

Comparative Example 3

The test was performed in the same manner as in Example 1 except that polyvinyl alcohol having an average degree of polymerization of 1,000 and a degree of saponification of 98 mol % was used as the synthetic resin.

Comparative Example 4

A polyacrylamide resin was obtained by mixing 100 parts by weight N-isopropylacrylamide, 75 parts by weight ethyl acetate and 0.5 parts by weight azobisisobutyronitrile, followed by polymerization at 65° C. for 8 hours under a nitrogen atmosphere. The prepared resin was measured for weight average molecular weight in terms of polystyrene by GPC method using "2690 Separations Model" manufactured by Waters Corporation as a column. The weight average molecular weight was about 90,000 (the degree of polymerization was about 800). The test was performed in the same manner as in Example 1 except that the obtained polyacrylamide resin was used as the synthetic resin.

Comparative Example 5

The test was performed in the same manner as in Comparative Example 4 except that 100 parts by weight ethyl acrylate was used instead of 100 parts by weight N-isopropylacrylamide. The weight average molecular weight of the obtained resin was about 60,000.

Comparative Example 6

The test was performed in the same manner as in Comparative Example 4 except that 100 parts by weight butyl methacrylate was used instead of 100 parts by weight N-isopropylacrylamide. The weight average molecular weight of the obtained resin was about 80,000.

Comparative Example 7

The test was performed in the same manner as in Example 3 except that 70 parts by weight N-vinylpyrrolidone was added to 30 parts by weight polyvinyl acetal. The weight average molecular weight of the obtained resin was about 90,000.

The obtained results are summarized in Tables 1 and 2.

TABLE 1

| | | Example 1 | Example 2 | Example 3 | Example 4 | Example 5 | Example 6 | Example 7 | Example 8 | Example 9 |
|---|---|---|---|---|---|---|---|---|---|---|
| Polyvinyl acetal resin | Degree of acetalization (mol %) | 77 | 76 | 70 | 65 | 54 | 70 | 70 | 70 | — |
| | Amount of acetyl group (mol %) | 1 | 1 | 1 | 1 | 1 | 1 | 1 | 1 | — |
| | Amount of hydroxyl group (mol %) | 20 | 21 | 28 | 25 | 21 | 27 | 27 | 27 | — |
| | Content of structural unit having amine structure (1) (mol %) | 0.3 | 0.3 | — | — | — | — | — | 2 | — |
| | Content of structural unit having imine structure (2) (mol %) | 1.7 | 1.7 | — | — | — | — | — | — | — |
| | Content of structural unit having amide structure (3) (mol %) | — | — | 1 | 9 | 24 | 2 | 2 | — | — |

TABLE 1-continued

|  |  | Example 1 | Example 2 | Example 3 | Example 4 | Example 5 | Example 6 | Example 7 | Example 8 | Example 9 |
|---|---|---|---|---|---|---|---|---|---|---|
| Poly (meth) acrylic ester | Total content of structural unit having amine structure, structural unit having imine structure and structural unit having amide structure ((1) + (2) + (3) (mol %) | 2 | 2 | 1 | 9 | 24 | 2 | 2 | 2 | — |
|  | Content of structural unit having amine structure (1) (mol %) | — | — | — | — | — | — | — | — | 5 |
|  | Content of structural unit having amide structure (3) (mol %) | — | — | — | — | — | — | — | — | — |
|  | Total content of structural unit having amine structure and structural unit having amide structure ((1) + (3)) (mol %) | — | — | — | — | — | — | — | — | 5 |
|  | Butyl methacrylate unit (mol %) | — | — | — | — | — | — | — | — | 11 |
|  | Ethyl acrylate unit (mol %) | — | — | — | — | — | — | — | — | 31 |
|  | Methyl methacrylate unit (mol %) | — | — | — | — | — | — | — | — | 53 |
| Properties of resin | Average degree of polymerization | 250 | 1600 | 250 | 250 | 250 | 250 | 250 | 250 | 800 |
|  | Nitrogen content (% by mass) | 0.7 | 0.7 | 0.5 | 3.5 | 8.1 | 0.6 | 0.6 | 0.7 | 0.9 |
| Evaluation for culture | Initial adhesion (iPS cell) | 8 | 8 | 9 | 9 | 7 | 5 | 6 | 6 | 6 |
|  | Cell proliferation (iPS cell) | 6 | 7 | 9 | 9 | 6 | 6 | 6 | 6 | 6 |
|  | Maintenance of adhesion (iPS cell) | 2 | 2 | 3 | 3 | 2 | 1 | 1 | 1 | 1 |
|  | Initial adhesion (hepatocyte) | ○○ | ○○ | ○○○ | ○○○ | ○○ | ○ | ○ | ○ | ○ |
|  | Cell proliferation (hepatocyte) | ○○ | ○○ | ○○○ | ○○○ | ○○ | ○ | ○ | ○ | ○ |

TABLE 2

|  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| Polyvinyl acetal resin | Degree of acetalization (mol %) | — | 40 | 0 | — | — | — | 21 |
|  | Amount of acetyl group (mol %) | — | 3 | 2 | — | — | — | 0 |
|  | Amount of hydroxyl group (mol %) | — | 57 | 98 | — | — | — | 8 |
|  | Content of structural unit having amine structure (1) (mol %) | — | — | — | — | — | — | — |
|  | Content of structural unit having imine structure (2) (mol %) | — | — | — | — | — | — | — |
|  | Content of structural unit having amide structure (3) (mol %) | — | — | — | — | — | — | 71 |
|  | Total content of structural unit having amine structure, structural unit having imine structure and structural unit having amide structure ((1) + (2) + (3) (mol %) | — | — | — | — | — | — | 71 |
| Poly (meth) acrylic ester | Content of structural unit having amine structure (1) (mol %) | — | — | — | — | — | — | — |
|  | Content of structural unit having amide structure (3) (mol %) | — | — | — | 100 | — | — | — |
|  | Total content of structural unit having amine structure and structural unit having amide structure ((1) + (3)) (mol %) | — | — | — | 100 | — | — | — |
|  | Content of structural unit derived from butyl methacrylate (mol %) | — | — | — | — | — | 100 | — |
|  | Content of structural unit derived from ethyl acrylate (mol %) | — | — | — | — | 100 | — | — |
|  | Content of structural unit derived from methyl methacrylate (mol %) | — | — | — | — | — | — | — |
| Properties of resin | Average degree of polymerization | — | 250 | 1000 | 800 | 600 | 550 | 250 |
|  | Nitrogen content (% by mass) | 0 | 0 | 0 | 12.2 | 0 | 0 | 10.2 |
| Evaluation for culture | Initial adhesion (iPS cell) | 3 | 4 | 3 | 2 | 2 | 4 | — |
|  | Cell proliferation (iPS cell) | 1 | 2 | 1 | 1 | 1 | 1 | — |
|  | Maintenance of adhesion (iPS cell) | 0 | 0 | 0 | 0 | 0 | 0 | — |
|  | Initial adhesion (hepatocyte) | x | x | x | x | x | x | x |
|  | Cell proliferation (hepatocyte) | x | x | x | x | x | x | x |

What is claimed is:

1. A container for culturing a cell, comprising a container body and a scaffolding material for culturing a cell arranged on the surface of the container body, the scaffolding material for culturing a cell being a resin film, wherein the scaffolding material for culturing a cell comprising a synthetic resin, the synthetic resin comprising a polyvinyl acetal resin, the polyvinyl acetal resin having a degree of acetalization of 65 mol % or more, and the synthetic resin having a nitrogen content of 0.1% by mass or more and 10% by mass or less.

2. The container for culturing a cell according to claim 1, wherein the synthetic resin contains a Bronsted basic group in an amount of 1 mol % or more and 50 mol % or less.

3. The container for culturing a cell according to claim 2, wherein the Bronsted basic group is an amine-based basic group.

4. The container for culturing a cell according to claim 2, wherein the synthetic resin contains at least one selected from the group consisting of a structural unit having an amine structure, a structural unit having an imine structure and a structural unit having an amide structure.

5. The container for culturing a cell according to claim 1, wherein the synthetic resin contains a structural unit having an amide structure.

6. The container for culturing a cell according to claim 1, wherein the synthetic resin contains both of a structural unit having an imine structure and a structural unit having an amine structure.

7. The container for culturing a cell according to claim 1, wherein the synthetic resin contains a polyvinyl butyral resin.

8. The container for culturing a cell according to claim 1, wherein the polyvinyl acetal resin has a degree of acetalization of 65 mol % or more and 90 mol % or less.

9. A carrier for culturing a cell, comprising: the scaffolding material for culturing a cell according to claim 1; and a polysaccharide.

10. A fiber for culturing a cell, comprising the scaffolding material for culturing a cell according to claim 1.

11. A method for culturing cells using the scaffolding material for culturing a cell according to claim 1.

* * * * *